United States Patent
Knappe et al.

(10) Patent No.: US 9,616,014 B2
(45) Date of Patent: Apr. 11, 2017

(54) HAIR COSMETICS

(71) Applicant: Henkel AG & Co. KGaA, Dusseldorf (DE)

(72) Inventors: Thorsten Knappe, Schenefeld (DE); Anna Henschel, Winsen (DE); Julia Bibane Lange, Sieversuetten (DE)

(73) Assignee: HENKEL AG & CO. KGAA, Dusseldorf (DE)

( * ) Notice: Subject to any disclaimer, the term of this patent is extended or adjusted under 35 U.S.C. 154(b) by 0 days.

(21) Appl. No.: 14/364,584

(22) PCT Filed: Nov. 9, 2012

(86) PCT No.: PCT/EP2012/072237
§ 371 (c)(1),
(2) Date: Jun. 11, 2014

(87) PCT Pub. No.: WO2013/087312
PCT Pub. Date: Jun. 20, 2013

(65) Prior Publication Data
US 2015/0007848 A1    Jan. 8, 2015

(30) Foreign Application Priority Data
Dec. 16, 2011    (DE) .................. 10 2011 088 841

(51) Int. Cl.
| | |
|---|---|
| *A61Q 5/06* | (2006.01) |
| *A61K 8/81* | (2006.01) |
| *A61K 8/02* | (2006.01) |
| *D21B 1/32* | (2006.01) |
| *A45D 7/04* | (2006.01) |
| *A45D 7/00* | (2006.01) |

(52) U.S. Cl.
CPC .............. *A61K 8/8182* (2013.01); *A45D 7/04* (2013.01); *A61K 8/022* (2013.01); *A61K 8/8152* (2013.01); *A61K 8/8158* (2013.01); *A61Q 5/06* (2013.01); *D21B 1/327* (2013.01); *A45D 2007/002* (2013.01); *A61K 2800/413* (2013.01); *A61K 2800/54* (2013.01); *A61K 2800/594* (2013.01); *A61K 2800/654* (2013.01); *Y02W 30/646* (2015.05)

(58) Field of Classification Search
None
See application file for complete search history.

(56) References Cited

U.S. PATENT DOCUMENTS

| | | | | |
|---|---|---|---|---|
| 8,021,651 | B2* | 9/2011 | Hentrich et al. ........... | 424/70.15 |
| 2001/0027171 | A1* | 10/2001 | Sajac ...................... | A61K 8/41 510/124 |
| 2005/0196364 | A1* | 9/2005 | Josso ................... | A61K 8/8158 424/59 |
| 2009/0226381 | A1* | 9/2009 | Maillefer ................ | A61Q 5/00 424/47 |

FOREIGN PATENT DOCUMENTS

| | | |
|---|---|---|
| DE | 102009002267 A1 | 10/2010 |
| EP | 1360955 A2 | 11/2003 |
| WO | 2007051511 A1 | 5/2007 |
| WO | 2007073857 A1 | 7/2007 |
| WO | WO 2009/023765 * | 2/2009 |
| WO | 2010054980 A1 | 5/2010 |
| WO | 2011076518 A1 | 6/2011 |

OTHER PUBLICATIONS

SEPINOV EMT 10 Product brochure (Feb. 2012).*
SEPPIC prodcut brochure on Sepinov EMT 10 (Apr. 2006).*
International Search Report completed Aug. 22, 2013 in PCT/EP2012/072237.

* cited by examiner

*Primary Examiner* — Jyothsna Venkat
(74) *Attorney, Agent, or Firm* — Lorenz & Kopf, LLP

(57) ABSTRACT

Cosmetic agents, in some embodiments in powder form, containing as component (a) at least one polymer comprising at least one structural unit of formula (I) and at least one structural unit of formula (II), in which X denotes a physiologically acceptable cation (in particular $Na^+$), $R^1$ denotes a hydrogen atom or a methyl group and $R^2$ denotes a ($C_2$ to $C_6$) hydroxyalkyl group, and as component (b) at least one setting polymer, are suitable for temporarily reshaping keratin-containing fibers. When applied to human hair, for example, an elastic hairstyle with volume was obtained. The hair retained its natural gloss.

15 Claims, No Drawings

HAIR COSMETICS

CROSS REFERENCE TO RELATED APPLICATIONS

The present disclosure is a U.S. National Stage entry under 35 U.S.C. §371 based on International Application No. PCT/EP2012/072237, filed Nov. 9, 2012, which claims priority to German Patent Application No. DE 10 2011 088 841.1 filed on Dec. 16, 2011, which is incorporated herein in its entirety by reference.

TECHNICAL FIELD

The technical field relates to keratin-containing fiber care, in particular to the temporary reshaping of keratin-containing fibers, such as for example temporary hair reshaping.

BACKGROUND

Styling agents for deforming keratin fibers have long been known and are used in various developments such as for example for volumizing, reviving and fixing of hairstyles, which with many hair types can only be achieved using setting active substances. Both hair treatment compositions which serve to shape hair permanently and those which shape it temporarily play an important role in this respect. Temporary shaping, which is intended to provide a good hold without impairing the healthy appearance of the hair, such as for example the gloss thereof, may be achieved for example by hairsprays, hair waxes, hair gels, setting lotions etc.

Appropriate agents for temporary shaping conventionally contain synthetic polymers as the shaping component. Preparations which contain a polymer may be applied to the hair by means of propellant gases or by a pump mechanism. Hair gels and hair waxes, on the other hand, are not generally applied directly onto the hair, but rather are distributed in the hair by means of a comb or the hands.

Known forms of temporary styling agents often cannot be dispensed with satisfactory accuracy. Thus, for instance, hair gels, hair creams and hair waxes are difficult to distribute once they have been applied to the hair. As soon as the comb or the hands onto which the styling composition has been applied come(s) into contact with the first bits of hair, comparatively large quantities of styling composition are released onto the hair. On the other hand, comparatively little styling composition is worked into bits of hair which are reached only later with the comb or the hands. The consequence of this is that the person applying the composition has either from the outset to apply a large quantity of styling composition, such that even those bits of hair which are reached last receive enough styling composition, or is obliged to apply the styling composition in a number of steps, wherein different bits of hair are treated each time. Hairsprays can be applied to hair more uniformly. However, since the user has no possibility of seeing the total quantity of styling composition applied, there is a risk of more styling composition being applied to the hair than is really necessary.

Pulverulent cosmetics are known and have already long been used for instance in the field of skin treatment. Typical examples are powder foundation or eyeshadow. To achieve the pulverulent consistency, it is necessary to use a pulverulent carrier material. A suitable carrier material may for instance be a metal oxide, such as for example silicon dioxide. However, the use of metal oxides as carrier material generally leads to deposition of the metal oxide on the keratin-containing fiber. Such deposition causes the keratin-containing fibers treated with such a pulverulent cosmetic preparation to lose their natural gloss and to take on a matt appearance. Moreover, a person skilled in the art is aware of pulverulent or granulated cosmetics for example from the field of hairdressing products. The hairdresser produces a defined quantity of the hair cosmetic from the powder or granular product by adding an excess of water, said hair cosmetic then being applied to the hair as a cream, gel or lotion. From the field of temporary reshaping keratin-containing fibers, a person skilled in the art is aware of solvent-containing powders in the form of a powder-to-liquid formulation. Document WO 2007/051511 A1 discloses the use of a pulverulent composition, containing 50 to 95 wt. % of an aqueous solvent, hydrophobized silicon dioxide powder and film-forming and/or setting polymer present at least in the aqueous solvent for temporary deformation of keratinic fibers.

Document WO 2010/054980 A1 discloses the use of a pulverulent composition with core-shell particles for temporary deformation of keratinic fibers, wherein the shell contains the particles of at least one hydrophobized metal oxide powder and the core comprises a liquid, aqueous phase. These pulverulent core-shell particles comprise at least one film-forming and/or setting polymer in the form of particles.

Document WO-A1-2011/076518 describes pulverulent compositions which may be converted into a liquid and which comprise an active substance sorbed onto a carrier.

Although prior art pulverulent hair cosmetics do deliver acceptable hold for hair reshaping, the result achieved with these agents is need of improvement with regard to the parameters of gloss and volume and hold elasticity. In addition, the known pulverulent compositions are not compatible with all cosmetic raw materials and exhibit limited storage stability.

SUMMARY

An object herein is to provide a hair treatment agent for temporary shaping which can be simply and precisely dispensed and provides the fibers with improved gloss and volume and an elastic hold. The durability of the styling result should also not be impaired. In an embodiment, the hair treatment agent is in powder form, and does not form lumps on contact with a small amount of water, but rather is readily distributable on the fibers.

DETAILED DESCRIPTION

It has been found that the prior art teaching is improved by a composition as described below, in particular in powder form. Compositions with the following requirements profile are novel with regard to application to the fibers in the context of reshaping keratin-containing fibers.

In accordance with a first exemplary embodiment, cosmetic agents are provided that comprise as component (a) at least one polymer comprising at least one structural unit of formula (I) and at least one structural unit of formula (II),

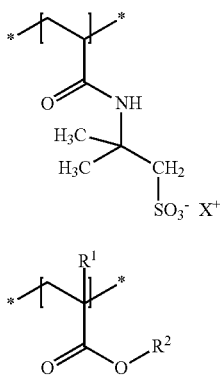

in which

X$^+$ denotes a physiologically acceptable cation (in particular Na$^+$),

R$^1$ denotes a hydrogen atom or a methyl group and

R$^2$ denotes a (C$_2$ to C$_6$) hydroxyalkyl group, and as component (b) at least one setting polymer.

As used herein, keratin-containing fibers should be understood to mean furs, wool, feathers and in particular human hair.

As used herein, polymers are compounds which are synthesized from a plurality of molecules, in which one kind or a plurality of species of atoms or atomic groups ("constitutive units", "basic building blocks" or "repeat units") are repeatedly arranged adjacent one another and have a molecular weight of at least about 10,000 g/mol. The polymers are obtained by polyreaction, wherein the latter may proceed artificially (i.e. synthetically) or naturally.

The structural unit of formula (I) is derived from 2-methyl-2[(1-oxo-2-propenyl)amino]-1-propanesulfonic acid (AMPS), which may be in partially or completely neutralized form. Conventionally Na$^+$ and NH$^{4+}$ are preferred as cations.

If, according to the above formula (II), the residue R$^2$ denotes a 2-hydroxyethyl group, the resultant component (a) polymers are most preferred.

Preferred component (a) polymers are obtainable under the INCI name Hydroxyethylacrylate/Sodium Acryloyldimethyl Taurate Copolymer for example in powder form from Seppic under the trade name Sepinov® EMT 10.

Irrespective of whether the agents contemplated herein contain one or more component (a) polymers, it is preferable to use these polymers within specific quantity ranges. In this case, preferred agents contemplated herein are those which contain said component (a) polymers in a quantity of between about 5 and about 95 wt. %, in particular of about 0.1 to about 50 wt. %, more preferably of about 5.0 to about 40.0 wt. % and particularly preferably of about 10.0 to about 30.0 wt. %, in each case relative to the weight of the agent.

Setting polymers assist in holding or building up the volume and fullness of the overall hairstyle. These polymers are simultaneously also film-forming polymers and therefore generally typical substances for shaping hair treatment agents such as hair setting preparations, hair mousses, hair waxes or hair sprays. Film formation may here take place only at points and connect only a few fibers together.

Film-forming compounds or film-forming polymers should be understood to mean those compounds/polymers which, on drying, leave behind a continuous film on the skin, hair or nails. Such film formers may be used in the most varied of cosmetic products, such as for example face masks, make-up, hair setting preparations, hairsprays, hair gels, hair waxes, hair tonics, shampoos or nail polishes.

Film-forming compounds or film-forming polymers are further understood to mean those polymers which are capable, when applied in an about 0.01 to about 20 wt. % aqueous, alcoholic or aqueous/alcoholic solution, of depositing a transparent film on the hair.

The setting polymers are preferably present in a quantity of about 2.0 wt. % to about 95 wt. %, in particular of about 5.0 wt. % to about 95.0 wt. %, particularly preferably of about 7.5 to about 95.0 wt. %, in each case relative to the total weight of the cosmetic agent.

Preferred cosmetic agents contain as component (b) setting polymer at least one setting polymer selected from polymers comprising at least one lactam structural unit. These polymers may in turn preferably be nonionic or cationic.

The pyrrolidon-1-yl group and the caprolactam-1-yl group may be mentioned as the lactam structural unit, wherein pyrrolidon-1-yl groups are more preferred as the lactam structural unit.

In the context of a particularly preferred embodiment, the cosmetic agents contemplated herein contain as film-forming component (b) polymer at least one nonionic setting polymer. This in turn preferably comprises at least one lactam structural unit.

In an exemplary embodiment, the nonionic setting polymers are present in the agent preferably in a quantity of about 2.0 wt. % to about 95 wt. %, in particular of about 5.0 wt. % to about 95.0 wt. % and particularly preferably of about 7.5 wt. % to about 95.0 wt. %, in each case relative to the weight of the agent.

The nonionic setting polymers are in turn preferably selected from at least one polymer from the group formed of
homopolymers and nonionic copolymers of N-vinylpyaolidone,
nonionic copolymers of isobutene,
nonionic copolymers of maleic anhydride.

Suitable polyvinylpyrrolidones are for example commercial products such as Luviskol® K 90 or Luviskol® K 85 from BASF SE. A suitable polyvinyl acetate is distributed for example under the trade name Vinac® as an emulsion by Air Products.

In some embodiments, agents containing as nonionic setting polymer at least one polymer selected from the group formed of
copolymer of maleic anhydride and methyl vinyl ether,
polyvinylpyrrolidone,
copolymers of N-vinylpyrrolidone and vinyl esters of carboxylic acids with 2 to 18 carbon atoms, in particular of N-vinylpyrrolidone and vinyl acetate,
or mixtures of these polymers, are particularly preferred. Those agents are in turn preferred which contain as nonionic setting polymer at least one polymer selected from the group formed of
polyvinylpyrrolidone,
copolymers of N-vinylpyrrolidone and vinyl esters of carboxylic acids with 2 to 18 carbon atoms, in particular of N-vinylpyrrolidone and vinyl acetate,
or mixtures of these polymers.

If copolymers of N-vinylpyrrolidone and vinyl esters of carboxylic acids with 2 to 18 carbon atoms, in particular of N-vinylpyrrolidone and vinyl acetate are used, it is in turn preferred for the molar ratio of the structural units obtained from the monomer N-vinylpyrrolidone to the structural units of the polymer obtained from the monomer vinyl esters of carboxylic acids with 2 to 18 carbon atoms (in particular vinyl acetate) to be in the range from about 20:80 to about 80:20, in particular from about 30:70 to about 60:40.

Suitable copolymers of vinylpyrrolidone and vinyl acetate are obtainable for example under the trademark Luviskol® VA 37, Luviskol® VA 55, Luviskol® VA 64 and Luviskol® VA 73 from BASF SE.

The cosmetic agents described herein preferably contain as film-forming component (b) polymer at least one cationic setting polymer. These in turn preferably comprise at least one lactam structural unit. For purposes herein, cationic polymers should be taken to mean polymers which comprise a group in the main and/or side chain which is "temporarily" or "permanently" cationic. Polymers which are designated "permanently cationic" are those which, irrespective of the pH value of the agent, comprise a cationic group. As a rule, these are polymers which contain a quaternary nitrogen atom, for example in the form of an ammonium group. Preferred cationic groups are quaternary ammonium groups. Polymers which have proven particularly suitable are those in which the quaternary ammonium group is attached via a $C_{1-4}$ hydrocarbon group to a main polymer chain synthesized from acrylic acid, methacrylic acid or the derivatives thereof.

A cationic setting polymer which is preferably suitable is at least one cationic setting polymer which contains at least one structural element of formula (M9) and optionally additionally at least one structural element of formula (M10),

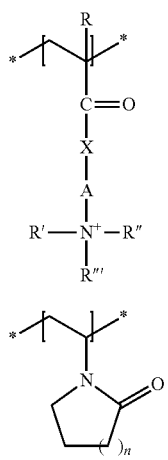

in which
R denotes a hydrogen atom or a methyl group,
R', R" and R'" independently from each other denote a ($C_1$ to $C_{30}$) alkyl group,
X denotes an oxygen atom or an NH group,
A denotes an ethane-1,2-diyl group or a propane-1,3-diyl group,
n means 1 or 3.

The positive polymer charge may be offset using any possible physiologically acceptable anions, such as for example chloride, bromide, hydrogensulfate, methylsulfate, ethylsulfate, tetrafluoroborate, phosphate, hydrogenphosphate, dihydrogenphosphate or p-toluenesulfonate, triflate.

At least one of the following compounds may preferably be used as said cationic setting polymer homopolymer of 2-(N,N,N-trimethylammoniumethyl) methacrylate (in particular the chloride with the INCI name Polyquaterium-37, for example under the trade name Ultragel 300 (BASF SE).

copolymers of diethylsulfate-quaternized dimethylaminoethylmethacrylate methosulfate with vinylpyrrolidone with the INCI name Polyquaternium-11 under the names Gafquat® 440, Gafquat® 734, Gafquat® 755 (in each case ISP) and Luviquat PQ 11 PN (BASF SE), copolymers of N-vinylpyrrolidone, N-(3-dimethylaminopropyl)methacrylamide and 3-(methacryloylamino) propyllauryldimethylammonium chloride (INCI name: Polyquaternium-55), which is sold for example under the trade name Styleze W 10 or W 20 (10 and 20 wt. % respectively of active substance in ethanol/water mixture) by ISP.

copolymers of N-vinylpyrrolidone, N-vinylcaprolactam, N-(3-dimethylaminopropyl)methacrylamide and 3-(methacryloylamino)propyllauryldimethylammonium chloride (INCI name: Polyquaternium-69), which is sold for example under the trade name AquaStyle® 300 (28-32 wt. % active substance in ethanol/water mixture) by ISP.

Cationic polymers which can more preferably be used in agents described herein are moreover those cationic setting copolymers which comprise at least one structural element of formula (M11)

(M11)

in which R" denotes a ($C_1$ to $C_4$) alkyl group, in particular a methyl group, and additionally comprise at least one further cationic and/or nonionic structural element.

The positive polymer charge may be offset using any possible physiologically acceptable anions, such as for example chloride, bromide, hydrogensulfate, methylsulfate, ethylsulfate, tetrafluoroborate, phosphate, hydrogenphosphate, dihydrogenphosphate or p-toluenesulfonate, triflate.

In an embodiment, it is in turn preferred for at least one copolymer (c1) to be present as additional cationic setting polymer, which copolymer (c1) additionally comprises a structural element of formula (M6) as well as at least one structural element of formula (M11), (M11)

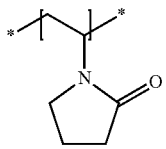

(M6)

in which R″ denotes a ($C_1$ to $C_4$) alkyl group, in particular a methyl group.

The positive polymer charge of the copolymers (c1) may be offset using any possible physiologically acceptable anions, such as for example chloride, bromide, hydrogensulfate, methylsulfate, ethylsulfate, tetrafluoroborate, phosphate, hydrogenphosphate, dihydrogenphosphate or p-toluenesulfonate, triflate.

Particularly preferred cationic setting polymers contain as copolymers (c1) about 10 to about 30 mol %, preferably about 15 to about 25 mol % and in particular about 20 mol % structural units according to formula (M11) and about 70 to about 90 mol %, preferably about 75 to about 85 mol % and in particular about 80 mol % structural units according to formula (M6).

In some embodiments, it is more preferred for the copolymers (c1) to contain, in addition to polymer units which arise from the incorporation of the stated structural units according to formula (M11) and (M6) into the copolymer, at most about 5 wt. %, preferably at most about 1 wt. %, polymer units originating from the incorporation of other monomers. The copolymers (c1) are preferably synthesized exclusively from structural units of formula (M11) with R″=methyl and (M6).

If a chloride ion is used to offset the positive charge of the polymer of formula (Poly1), these N-methylvinylimidazole/vinylpyrrolidone copolymers are designated in accordance with INCI nomenclature as Polyquaternium-16 and are obtainable for example from BASF under the trade names Luviquat® Style, Luviquat® FC 370, Luviquat® FC 550, Luviquat® FC 905 and Luviquat® MQ 552

If a methosulfate is used to offset the positive charge of the polymer of formula (Poly1), these N-methylvinylimidazole/vinylpyrrolidone copolymers are designated in accordance with INCI nomenclature as Polyquaternium-44 and are obtainable for example from BASF under the trade name Luviquat® UltraCare.

In addition to or instead of the copolymer(s) (c1), in some embodiments cosmetic agents may also contain copolymers (c2) which, on the basis of copolymer (c1), comprise structural units of formula (M7) as additional structural units

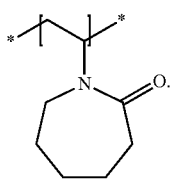

(M7)

Further cosmetic agents which are more preferred are thus characterized in that they contain as cationic setting polymer at least one copolymer (c2) which contains at least one structural unit according to formula (M11-a) and at least one structural unit according to formula (M6) and at least one structural unit according to formula (M7)

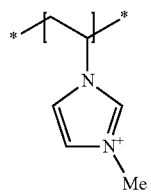

(M11-a)

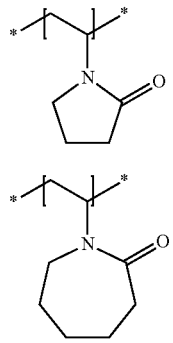

(M6)

(M7)

In this case too, it is more preferred for the copolymers (c2) to contain, in addition to polymer units which arise from the incorporation of the stated structural units according to formula (M11-a), (M6) and (M7) into the copolymer, at most about 5 wt. %, preferably at most about 1 wt. %, polymer units originating from the incorporation of other monomers. The copolymers (c2) are preferably synthesized exclusively from structural units of formulae (M11-a), (M6) and (M7).

The positive polymer charge of component (c2) may be offset using any possible physiologically acceptable anions, such as for example chloride, bromide, hydrogensulfate, methylsulfate, ethylsulfate, tetrafluoroborate, phosphate, hydrogenphosphate, dihydrogenphosphate or p-toluenesulfonate, triflate.

If a methosulfate is used to offset the positive charge of the polymer of formula (Poly2), such N-methylvinylimidazole/vinylpyrrolidone/vinylcaprolactam copolymers are designated in accordance with INCI nomenclature as Polyquaternium-46 and are obtainable for example from BASF under the trade name Luviquat® Hold.

In some embodiments, particularly preferred copolymers (c2) contain about 1 to about 20 mol %, preferably about 5 to about 15 mol % and in particular about 10 mol % structural units according to formula (M11-a) and about 30 to about 50 mol %, preferably about 35 to about 45 mol % and in particular about 40 mol % structural units according to formula (M6) and about 40 to about 60 mol %, preferably about 45 to about 55 mol % and in particular about 60 mol % structural units according to formula (M7).

In addition to or instead of the copolymer(s) (c1) and/or (c2), in some embodiments the cosmetic agents may also contain copolymers (c3) as a cationic setting polymer, which copolymers (c3) contain structural units of the formulae (M11-a) and (M6) as structural units, together with further structural units from the group of vinylimidazole units and further structural units from the group of acrylamide and/or methacrylamide units.

In some embodiments, further cosmetic agents which are particularly preferred are thus characterized in that they contain as additional cationic setting polymer at least one copolymer (c3) which contains at least one structural unit according to formula (M11-a) and at least one structural unit according to formula (M6) and at least one structural unit according to formula (M10) and at least one structural unit according to formula (M12).

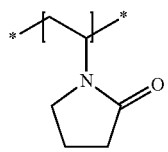
(M11-a)

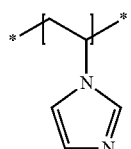
(M6)

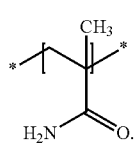
(M8)

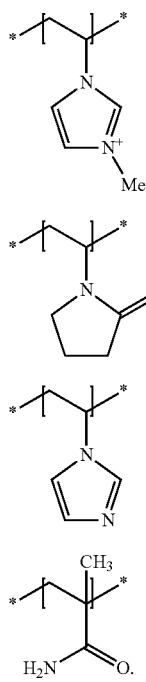
(M12)

In this case too, it is more preferred for the copolymers (c3) to contain, in addition to polymer units which arise from the incorporation of the stated structural units according to formula (M11-a), (M6), (M8) and (M12) into the copolymer, at most about 5 wt. %, preferably at most about 1 wt. %, polymer units originating from the incorporation of other monomers. The copolymers (c3) are preferably synthesized exclusively from structural units of formulae (M11-a), (M6), (M8) and (M12).

The positive polymer charge of component (c3) may be offset using any possible physiologically acceptable anions, such as for example chloride, bromide, hydrogensulfate, methylsulfate, ethylsulfate, tetrafluoroborate, phosphate, hydrogenphosphate, dihydrogenphosphate or p-toluenesulfonate, triflate.

If a methosulfate is used to offset the positive charge of the polymer of formula (Poly3), such N-methylvinylimidazole/vinylpyrrolidone/vinylimidazole/methacrylamide copolymers are designated in accordance with INCI nomenclature as Polyquaternium-68 and are obtainable for example from BASF under the trade name Luviquat® Supreme.

In some embodiments, particularly preferred copolymers (c3) contain about 1 to about 12 mol %, preferably about 3 to about 9 mol % and in particular about 6 mol % structural units according to formula (M11-a) and about 45 to about 65 mol %, preferably about 50 to about 60 mol % and in particular about 55 mol % structural units according to formula (M6) and about 1 to about 20 mol %, preferably about 5 to about 15 mol % and in particular about 10 mol % structural units according to formula (M8) and about 20 to about 40 mol %, preferably about 25 to about 35 mol % and in particular about 29 mol % structural units according to formula (M12).

Further more preferred cosmetic agents are characterized in that they contain as cationic setting polymer at least one copolymer (c4) comprising at least one structural unit of formula (M6), at least one structural unit of formula (M13), at least one structural unit of formula (M8) and at least one structural unit of formula (M11),

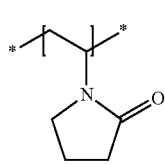
(M6)

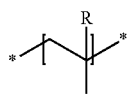
(M13)

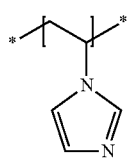
(M8)

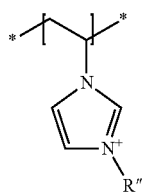
(M11)

in which

R" denotes a ($C_1$ to $C_4$) alkyl group, in particular a methyl group,

R denotes a hydrogen atom or a methyl group,

R'" denotes a hydrogen atom or an equivalent of a physiologically acceptable cation.

Any physiologically acceptable anion (such as for example chloride, bromide, hydrogensulfate, methylsulfate, ethylsulfate, tetrafluoroborate, phosphate, hydrogenphosphate, dihydrogenphosphate or p-toluenesulfonate, triflate) may serve to offset the positive charge of the structural unit (IV).

Examples of ($C_1$ to $C_4$) alkyl groups are methyl, ethyl, propyl, isopropyl, butyl, sec-butyl, isobutyl and tert-butyl.

In some embodiments, it is preferable for said copolymer to have a charge density of the cationic charge of about 0.8 meq/g at a pH value of about 7.

It is preferable for R according to formula (M13) to denote a methyl group. It is preferable for R'" according to formula (M13) to denote a hydrogen atom. It is preferable for R" according to formula (M11) to denote a methyl group.

In some embodiments, a copolymer which is more preferred comprises at least one structural unit of formula (M6), at least one structural unit of formula (M13-a), at least one structural unit of formula (M8) and at least one structural unit of formula (M11-a).

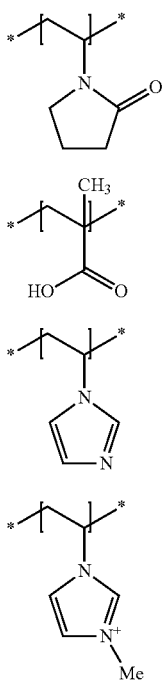

(I)

(M13-a)

(M11-a)

In some related embodiments, the agents contain a copolymer of N-vinylpyrrolidone, N-vinylimidazole, N-methyl-N'-vinylimidazolium chloride and methacrylic acid as said copolymer.

In further related embodiments, it is most preferable for the copolymer bearing the INCI name Polyquaternium-86 to be present as the copolymer in the agents. INCI is an abbreviation for International Nomenclature of Cosmetic Ingredients. Such copolymers are sold for example by BASF SE under the trade name Luvigel® Advanced in the form of a white powder.

Among the setting polymers selected from the cationic polymers with at least one structural element of the above formula (M11-a), the following are preferred:

- vinylpyrrolidone/1-vinyl-3-methyl-1H-imidazolium chloride copolymers (such as for example that with the INCI name Polyquaternium-16 under the trade names Luviquat® Style, Luviquat® FC 370, Luviquat® FC 550, Luviquat® FC 905 and Luviquat® MQ 552 (BASF SE)),
- vinylpyrrolidone/1-vinyl-3-methyl-1H-imidazolium methylsulfate copolymers (such as for example that with the INCI name Polyquaternium-44 under the trade name Luviquat® Care (BASF SE)),
- vinylpyrrolidone/vinylcaprolactam/1-vinyl-3-methyl-1H-imidazolium terpolymer (such as for example that with the INCI name Polyquaternium-46 under the trade names Luviquat® Care or Luviquat® Hold (BASF SE)),
- vinylpyrrolidone/methacrylamide/vinylimidazole/1-vinyl-3-methyl-1H-imidazolium methylsulfate copolymer (such as for example that with the INCI name Polyquaternium-68 under the trade name Luviquat® Supreme (BASF SE)),
- copolymer of N-vinylpyrrolidone, N-vinylimidazole, N-methyl-N'-vinylimidazolium chloride and methacrylic acid (such as for example that with the INCI name Polyquaternium-86 under the trade name Luvigel® Advanced (BASF SE)), and mixtures of these polymers.

Further cationic polymers preferably usable in the cosmetic agents described herein are "temporarily cationic" polymers. These polymers conventionally contain an amino group which at specific pH values is in the form of a quaternary ammonium group and is thus cationic.

Particularly preferred cosmetic agents contain as component (b) setting polymer at least one setting polymer which comprises at least one structural unit of formula (III) and at least one structural unit of formula (IV),

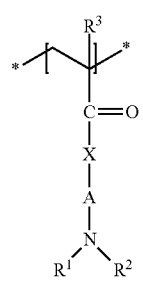

(III)

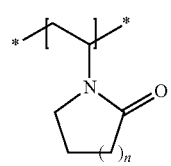

(IV)

in which n denotes 1, 2 or 3, $R^1$ and $R^2$ independently from each other denote a ($C_1$ to $C_6$) alkyl group (in particular methyl)

A denotes ethane-1,2-diyl or propane-1,3-diyl,

X denotes an oxygen atom or an NH group, $R^3$ denotes a hydrogen atom or methyl.

Component (b) setting polymers preferably suitable are those which comprise as structural unit of formula (IV) at least one structural unit of formulae (M1-1) to (M1-8)

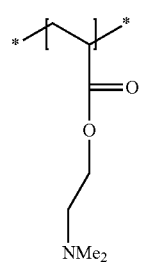

(M1-1)

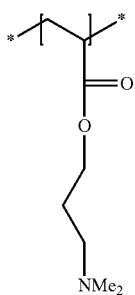
(M1-2)

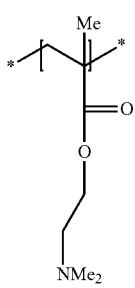
(M1-3)

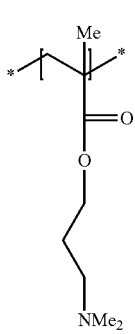
(M1-4)

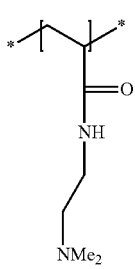
(M1-5)

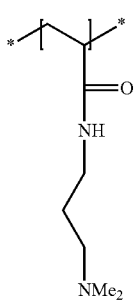
(M1-6)

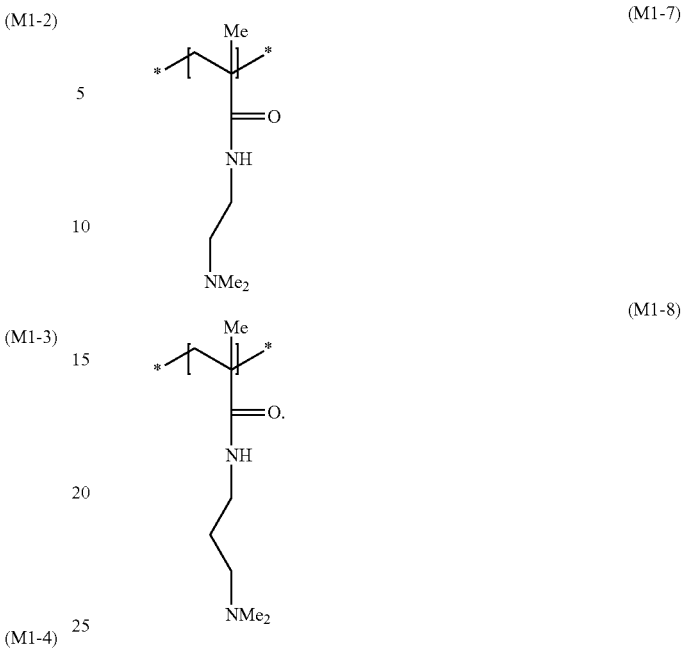

Here, the group of polymers
vinylcaprolactam/vinylpyrrolidone/dimethylaminoethyl methacrylate copolymer (for example INCI name: Vinyl Caprolactam/PVP/Dimethylaminoethyl Methacrylate Copolymer under the trade name Gaffix® VC 713 (ISP)),
vinylpyrrolidone/vinylcaprolactam/dimethylaminopropylmethacrylamide copolymer (for example INCI name: VP/Vinyl Caprolactam/DMAPA Acrylates Copolymer, under the trade name Aquaflex® SF-40 (ISP)),
vinylcaprolactam/vinylpyrrolidone/dimethylaminoethyl methacrylate copolymer (for example as powder in the form of the commercial product Advantage S bearing the INCI name: Vinyl Caprolactam/VP/Dimethylaminoethyl Methacrylate Copolymer (ISP)),
vinylpyrrolidone/dimethylaminopropylmethacrylamide copolymer (for example INCI name: VP/DMAPA Acrylates Copolymer, under the trade name Styleze CC-10 (ISP)),
again serves as a preferred list for selection of at least one or more setting polymers therefrom.

In some embodiments, the cationic polymers are present in quantities of about 2.0 wt. % to about 95 wt. %, in particular of about 5.0 wt. % to about 95.0 wt. %, particularly preferably of about 7.5 to about 95.0 wt. %, in each case relative to the total weight of the cosmetic agents.

The cosmetic agents described herein may also contain as setting polymer at least one amphoteric setting polymer. The term amphoteric polymers as used herein includes not only those polymers which contain in each molecule both free amino groups and free —COOH or SO₃H groups and are capable of forming internal salts, but also zwitterionic polymers, which contain in each molecule quaternary ammonium groups and —COO⁻ or —SO₃⁻ groups, and those polymers which contain —COOH or SO₃H groups and quaternary ammonium groups.

One example of an amphoteric polymer is the acrylic resin obtainable under the name Amphomer®, which is a copolymer of tert-butylaminoethyl methacrylate, N-(1,1,3,3-tetramethylbutyl)acrylamide and two or more monomers from the group acrylic acid, methacrylic acid and the simple alkyl esters thereof.

Furthermore, at least one anionic setting polymer may preferably be used as component (b) setting polymers. The anionic polymers are anionic polymers which preferably comprise carboxylate and/or sulfonate groups. Examples of anionic monomers of which such polymers may consist are acrylic acid, methacrylic acid, crotonic acid, maleic anhydride and 2-acrylamido-2-methylpropanesulfonic acid. In this case, the acidic groups may wholly or in part be in the form of a sodium, potassium, ammonium, mono- or triethanolammonium salt.

Within this embodiment it is preferable to use copolymers of at least one anionic monomer and at least one nonionogenic monomer. With regard to anionic monomers, reference is made to the above-listed substances. Preferred nonionogenic monomers are acrylamide, methacrylamide, acrylic acid esters, methacrylic acid esters, vinylpyrrolidone, vinyl ethers and vinyl esters.
Preferred anionic copolymers are acrylic acid-acrylamide copolymers and in particular polyacrylamide copolymers with monomers containing sulfonic acid groups. A more preferred anionic copolymer consists of about 70 to about 55 mol % acrylamide and about 30 to about 45 mol % 2-acrylamido-2-methylpropanesulfonic acid, wherein the sulfonic acid group is wholly or in part in the form of a sodium, potassium, ammonium, mono- or triethanolammonium salt. Further anionic polymers which may preferably be used are selected from the group formed of
- copolymers of vinyl acetate and crotonic acid (as are marketed for example by CIBA as commercial product Aristoflex® A 60 under the INCI name VA/Crotonates Copolymer in a 60 wt. % dispersion in isopropanol/water),
- copolymers of ethyl acrylate and methacrylic acid (as sold for example under the trade name Luviflex® Soft with an acid value of 84 to 105 under the INCI name Acrylates Copolymer in an approximately 20 to 30 wt. % dispersion in water by BASF SE),
- polyurethanes with at least one carboxyl group (such as for example a copolymer of isophthalic acid, adipic acid, 1,6-hexanediol, neopentyl glycol and isophorone diisocyanate as sold under the trade name Luviset PU with the INCI name Polyurethane-1 by BASF SE).

It is moreover preferred for a cosmetic agent to contain relative to its weight no more than about 8 wt. %, in particular no more than about 5 wt. %, of a liquid.

More preferably, the cosmetic agents described herein are in powder form. As used herein, cosmetic agents are pulverulent if their particles flow freely under their own weight (cf. DIN EN ISO 6186: 1998-08). As used herein, particles are grains (cf. DIN 66160: 1992-09) of solids.

It should explicitly be noted that the representatives of components (a) and (b) of the agent mentioned previously as being preferred (see above) are more preferred for the embodiment as powder.

In the context of the embodiment of agents as powder, it has again proven particularly advantageous for the volume-related average particle diameter ($d_{0.5}$ volume related, determined by laser diffraction) of the powder to be in a range from about 10 μm to about 800 μm, in particular from about 25 μm to about 500 μm.

As used herein, keratin-containing fibers should be understood to mean furs, wool, feathers and in particular human hair.

In some embodiments, the agents in powder form are very simple to dispense. In related embodiments, they may be distributed very uniformly over the keratin-containing fibers in the presence of a small amount of water, i.e. by previous application to a damp surface of an application aid and/or by application to damp hair. The small quantity of solvent on the damp hair or the damp surface of an application aid is sufficient for targeted wetting of the hair fibers with the cosmetic preparation. Lumps do not form.

In some embodiments, the agents, in particular in embodiments where the agent is a powder, may additionally contain at least one wax. In some related embodiments, waxes used in cosmetic agents described herein exhibit a melting point at about 1013 mbar in a range from about 38° C. to about 95° C.

The waxes are preferably selected from vegetable, animal and mineral waxes, wherein preferred waxes are those which have a melting point in the range from about 50° C. to about 90° C.

In some embodiments, it is more preferred for the cosmetic agent to contain at least one wax, selected from the group formed of beeswax (Cera Alba), carnauba wax, candelilla wax, rice bran wax, montan wax, paraffin wax, microcrystalline paraffin wax, ozokerite wax and cetyl palmitate.

In some embodiments, a plurality of waxes may also be used. For instance, an addition of carnauba wax may be used to increase the melting and dropping point of another wax and to reduce its tackiness. A series of wax mixtures, optionally in a blend with further additives, is accordingly commercially available. Examples of the mixtures preferably used are "Spezialwachs 7686 OE" (a mixture of cetyl palmitate, beeswax, microcrystalline wax and polyethylene with a melting range of 73-75° C.; manufacturer: Kahl & Co), Kahlwax 6240 (hydrogenated vegetable oil) and "Weichceresin® FL 400" (a vaseline/vaseline oil/wax mixture with a melting point of 50-54° C.; manufacturer: Parafluid Mineralölgesellschaft).

It has proven more preferable for wax-containing agents to contain, together with at least one wax, in addition at least one emulsifier. In the context of this embodiment, liquid emulsifiers may also be used, providing these yield a pulverulent compound for example by sorption when blended with the at least one wax.

Preferred emulsifiers are nonionic and contain as hydrophilic group for example a polyol group, a polyalkylene glycol ether group or a combination of a polyol group and polyglycol ether group. In some embodiments, the cosmetic agent preferably additionally contains, in addition to at least one wax, at least one nonionic emulsifier selected from at least one compound from the group formed of
- addition products of about 2 to about 100 mol ethylene oxide and/or about 1 to about 5 mol propylene oxide onto saturated or unsaturated, linear or branched fatty alcohols with 8 to 30 C atoms and onto fatty acids with 8 to 30 C atoms,
- addition products of 2 to 50 mol ethylene oxide and/or 1 to 5 mol propylene oxide end group-terminated with a methyl or $C_2$-$C_6$ alkyl residue onto linear and branched fatty alcohols with 8 to 30 C atoms, onto fatty acids with 8 to 30 C atoms and onto alkylphenols with 8 to 15 C atoms in the alkyl group, such as for example the grades obtainable under the commercial names Dehydol® LS and Dehydol® PS (Cognis),
- $C_{12}$-$C_{30}$ fatty acid mono- and diesters of addition products of 1 to 30 mol of ethylene oxide onto glycerol, addition products of about 5 to about 60 mol ethylene oxide onto castor oil and hardened castor oil, polyol fatty acid esters, such as for example the commercial product Hydagen® HSP (Cognis) or Sovermol grades (Cognis), alkoxylated triglycerides, alkoxylated fatty acid alkyl esters of formula (E4-I)

$R^1CO—(OCH2CHR^2)_w OR^3$ (E4-I)

in which $R^1CO$ denotes a linear or branched, saturated and/or unsaturated acyl residue having 6 to 22 carbon atoms, $R^2$ denotes hydrogen or methyl, $R^3$ denotes linear or branched alkyl residues having 1 to 4 carbon atoms and w denotes numbers from 1 to 20, amine oxides, hydroxy mixed ethers, sorbitan fatty acid esters and addition products of ethylene oxide onto sorbitan fatty acid esters such as for example polysorbates, sugar fatty acid esters and addition products of ethylene oxide onto sugar fatty acid esters, addition products of ethylene oxide onto fatty acid alkanolamides and fatty amines, sugar surfactants of the alkyl and alkenyl oligoglycoside type according to formula (E4-II),

$R^4O—[G]_p$ (E4-II)

in which $R^4$ denotes an alkyl or alkenyl residue having 4 to 22 carbon atoms, G denotes a sugar residue having 5 or 6 carbon atoms and p denotes numbers from 1 to 10.

In some embodiments where the agents are in pulverulent solid form, they may additionally contain pulverulent metal oxides. These metal oxides may be hydrophilic or hydrophobic.

Metal oxides which are preferably suitable are selected from at least one representative of the group formed of silicates, aluminum silicates, titanium dioxide, zinc oxide and silicon dioxide.

More preferred aluminum silicates (also known as aluminosilicates) are selected from among phyllosilicates, tectosilicates or mixtures thereof.

Preferably suitable phyllosilicates are selected from among kaolins (here in particular kaolinite, dickite, halloysite and nacrite), serpentine, talcum, pyrophyllite, montmorillonite, quartz, bentonite, mica (here in particular illite, muscovite, paragonite, phlogopite, biotite, lepidolite, margarite and smectite (here in particular montmorrilionite, saponite, nontronite and hectorite)).

Preferably suitable tectosilicates are selected from among feldspar minerals (in particular albite, orthoclase, anorthite, leucite, sodalite, hauyne, labradorite, lazurite, nosean, nepheline) and zeolites.

In embodiments where the agents are in pulverulent solid form, they may additionally contain pulverulent salts. Phosphates are suitable in this case, provided it is not necessary to avoid such use for environmental reasons. Among the numerous commercially obtainable phosphates, the alkali metal phosphates are very suitable, with particular preference given to pentasodium or pentapotassium triphosphate (sodium or potassium tripolyphosphate).

"Alkali metal phosphates" is the generic name for the alkali metal (in particular sodium and potassium) salts of the various phosphoric acids, a distinction being drawn between meta-phosphoric acids $(HPO_3)_n$ and ortho-phosphoric acid $H_3PO_4$ as well as higher molecular weight representatives. Examples of such phosphates are pentasodium triphosphate, $Na_5P_3O_{10}$ (sodium tripolyphosphate) and the corresponding potassium salt pentapotassium triphosphate, $K_5P_3O_{10}$ (potassium tripolyphosphate). Sodium potassium tripolyphosphates are also preferably used.

Mineral salts of monovalent metal ions, such as for example $Na_2SO_4$ or sodium chloride have also proven suitable.

In embodiments where the agents are in pulverulent solid form, they may additionally contain dextrins, such as for example oligomers or polymers of carbohydrates, which may be obtained by partial hydrolysis of starches. Hydrolysis may be carried out in accordance with conventional, for example acid- or enzyme-catalyzed, methods. The hydrolysis products are preferably those with average molar masses in the range from about 400 to about 500000 g/mol. A polysaccharide with a dextrose equivalent (DE) in the range from about 0.5 to about 40, in particular from about 2 to about 30 is here preferred, wherein DE is a conventional measure of the reducing action of a polysaccharide in comparison with dextrose, which has a DE of about 100. Usable compounds are not only maltodextrins with a DE of between about 3 and about 20 and dry glucose syrups with a DE of between about 20 and about 37 but also "yellow" and "white" dextrins with higher molar masses in the range from about 2000 to about 30000 g/mol.

The oxidized derivatives of such dextrins are the reaction products thereof with oxidizing agents which are capable of oxidizing at least one alcohol function of the saccharide ring to yield a carboxylic acid function.

Embodiments (A) to (H) are particularly preferred:

(A): a pulverulent cosmetic agent containing as component
(a) at least one polymer comprising at least one structural unit of formula (I) and at least one structural unit of formula (II),

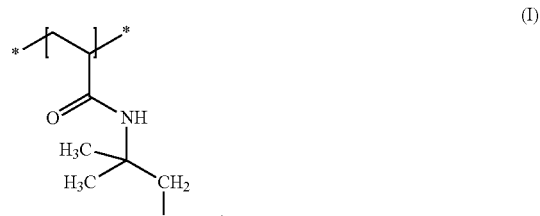

(I)

(II)

in which $X^+$ denotes a physiologically acceptable cation (in particular $Na^+$), $R^1$ denotes a hydrogen atom or a methyl group and $R^2$ denotes a ($C_2$ to $C_6$) hydroxyalkyl group, and as component (b) at least one setting polymer comprising at least one lactam structural unit.

(B): a pulverulent cosmetic agent containing as component
(a) at least one polymer comprising at least one structural unit of formula (I) and at least one structural unit of formula (II), (I)

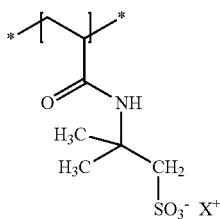

(II)

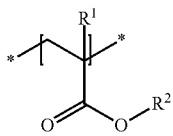

in which X⁺ denotes a physiologically acceptable cation (in particular Na⁺),
R¹ denotes a hydrogen atom or a methyl group and
R² denotes a ($C_2$ to $C_6$) hydroxyalkyl group,
and as component (b) at least one setting polymer comprising at least one structural unit of formula (III) and at least one structural unit of formula (IV), (III)

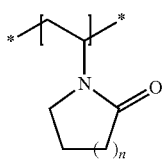

(IV)

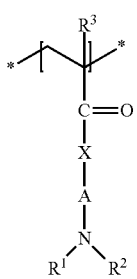

in which n denotes 1, 2 or 3,
R¹ and R² independently from each other denote a ($C_1$ to $C_6$) alkyl group (in particular methyl)
A denotes ethane-1,2-diyl or propane-1,3-diyl,
X denotes an oxygen atom or an NH group,
R³ denotes a hydrogen atom or methyl.

(C): a pulverulent cosmetic agent containing as component (a) at least one polymer comprising at least one structural unit of formula (I) and at least one structural unit of formula (II), (I)

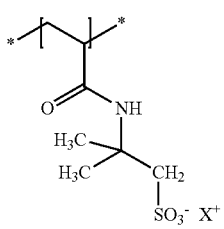

(II)

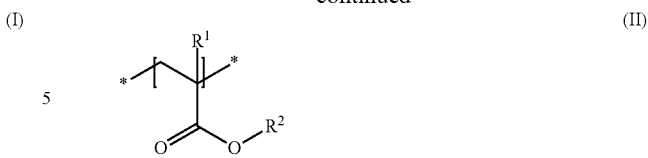

in which X⁺ denotes a physiologically acceptable cation (in particular Na⁺),
R¹ denotes a hydrogen atom or a methyl group and
R² denotes 2-hydroxyethyl,
and as component (b) at least one setting polymer comprising at least one lactam structural unit.

(D): a pulverulent cosmetic agent containing as component (a) at least one polymer comprising at least one structural unit of formula (I) and at least one structural unit of formula (II), (I)

(II)

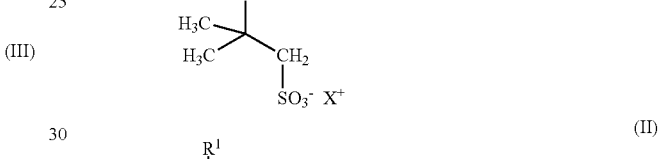

in which X⁺ denotes a physiologically acceptable cation (in particular Na⁺),
R¹ denotes a hydrogen atom or a methyl group and
R² denotes 2-hydroxyethyl,
and as component (b) at least one setting polymer comprising at least one structural unit of formula (III) and at least one structural unit of formula (IV), (III)

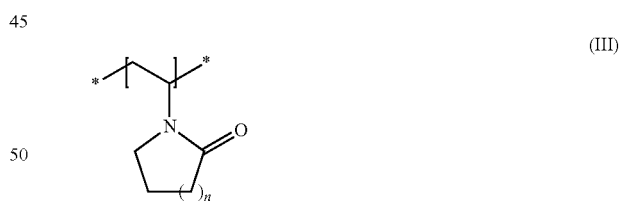

(IV)

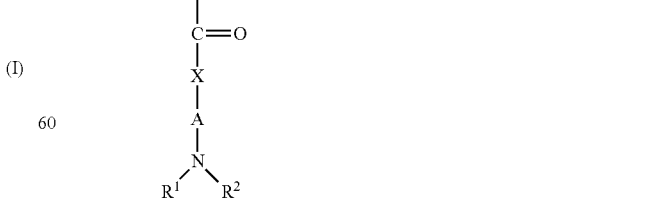

in which n denotes 1, 2 or 3,
R¹ and R² independently from each other denote a ($C_1$ to $C_6$) alkyl group (in particular methyl)

A denotes ethane-1,2-diyl or propane-1,3-diyl,
X denotes an oxygen atom or an NH group,
$R^3$ denotes a hydrogen atom or methyl.

(E): a pulverulent cosmetic agent containing as component (a), relative to the total weight of the cosmetic agent, from about 2.0 wt. % to about 95 wt. %, in particular from about 5.0 wt. % to about 95.0 wt. %, more preferably from about 7.5 to about 95.0 wt. % of at least one polymer comprising at least one structural unit of formula (I) and at least one structural unit of formula (II),

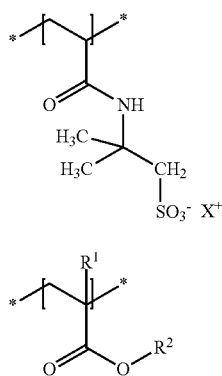

(I)

(II)

in which $X^+$ denotes a physiologically acceptable cation (in particular $Na^+$),
$R^1$ denotes a hydrogen atom or a methyl group and
$R^2$ denotes a ($C_2$ to $C_6$) hydroxyalkyl group,
and as component (b) about 5 and about 95 wt. %, in particular from about 0.1 to about 50 wt. %, more preferably from about 5.0 to about 40.0 wt. % and particularly preferably from about 10.0 to about 30.0 wt. % of at least one setting polymer, comprising at least one lactam structural unit.

(F): a pulverulent cosmetic agent containing as component (a), relative to the total weight of the cosmetic agent, from about 2.0 wt. % to about 95 wt. %, in particular from about 5.0 wt. % to about 95.0 wt. %, more preferably from about 7.5 to about 95.0 wt. % of at least one polymer comprising at least one structural unit of formula (I) and at least one structural unit of formula (II),

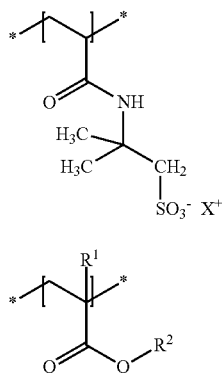

(I)

(II)

in which $X^+$ denotes a physiologically acceptable cation (in particular $Na^+$), $R^1$ denotes a hydrogen atom or a methyl group and
$R^2$ denotes a ($C_2$ to $C_6$) hydroxyalkyl group,
and as component (b) about 5 and about 95 wt. %, in particular from about 0.1 to about 50 wt. %, more preferably from about 5.0 to about 40.0 wt. % and particularly preferably from about 10.0 to about 30.0 wt. % of at least one setting polymer, comprising at least one structural unit of formula (III) and at least one structural unit of formula (IV),

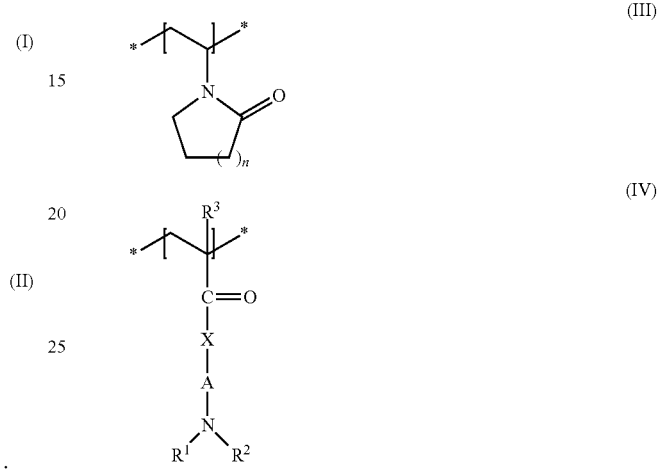

(III)

(IV)

in which n denotes 1, 2 or 3,
$R^1$ and $R^2$ independently from each other denote a ($C_1$ to $C_6$) alkyl group (in particular methyl)
A denotes ethane-1,2-diyl or propane-1,3-diyl,
X denotes an oxygen atom or an NH group,
$R^3$ denotes a hydrogen atom or methyl.

(G): a pulverulent cosmetic agent containing as component (a), relative to the total weight of the cosmetic agent, from 2.0 wt. % to 95 wt. %, in particular from 5.0 wt. % to 95.0 wt. %, more preferably from 7.5 to 95.0 wt. % of at least one polymer comprising at least one structural unit of formula (I) and at least one structural unit of formula (II),

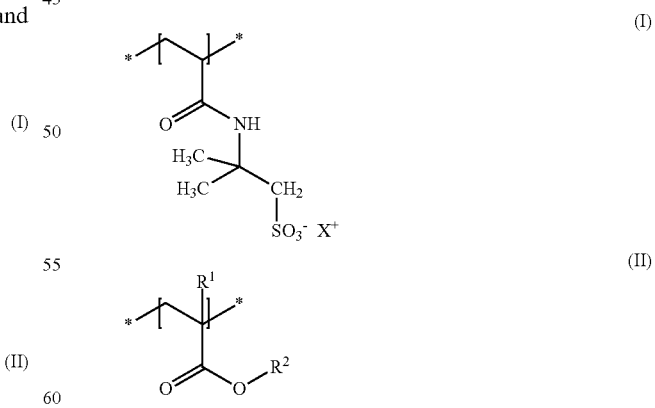

(I)

(II)

in which $X^+$ denotes a physiologically acceptable cation (in particular $Na^+$),
$R^1$ denotes a hydrogen atom or a methyl group and
$R^2$ denotes 2-hydroxyethyl,
and as component (b) about 5 and about 95 wt. %, in particular from about 0.1 to about 50 wt. %, more preferably from about 5.0 to about 40.0 wt. % and particularly preferably from about 10.0 to about 30.0 wt. % of at least one setting polymer, comprising at least one lactam structural unit.

(H): a pulverulent cosmetic agent containing as component (a), relative to the total weight of the cosmetic agent, from about 2.0 wt. % to about 95 wt. %, in particular from about 5.0 wt. % to about 95.0 wt. %, more preferably from about 7.5 to about 95.0 wt. % of at least one polymer comprising at least one structural unit of formula (I) and at least one structural unit of formula (II),

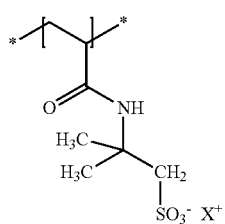
(I)

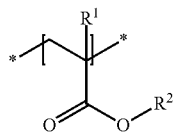
(II)

in which $X^+$ denotes a physiologically acceptable cation (in particular $Na^+$), $R^1$ denotes a hydrogen atom or a methyl group and $R^2$ denotes 2-hydroxyethyl, and as component (b) about 5 and about 95 wt. %, in particular from about 0.1 to about 50 wt. %, more preferably from about 5.0 to about 40.0 wt. % and particularly preferably from about 10.0 to about 30.0 wt. % of at least one setting polymer, comprising at least one structural unit of formula (III) and at least one structural unit of formula (IV),

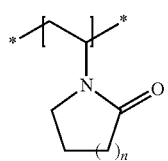
(III)

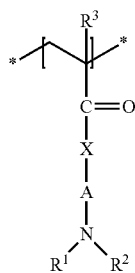
(IV)

in which n denotes 1, 2 or 3, $R^1$ and $R^2$ independently from each other denote a ($C_1$ to $C_6$) alkyl group (in particular methyl)

A denotes ethane-1,2-diyl or propane-1,3-diyl,

X denotes an oxygen atom or an NH group, $R^3$ denotes a hydrogen atom or methyl.

For embodiments (A) to (H) the embodiments of the features stated therein and described above as preferred (see above) are mutatis mutandis likewise preferable. Moreover, the average particle diameters stated as preferred are preferred in the context of embodiments (A) to (H).

The cosmetic agents described herein may be packaged in virtually any desired containers. It has merely to be ensured that, on discharge of the agent, the powder is not exposed to a mechanical load which is so great that the powder is transformed into liquid form as early as the time of discharge. Suitable containers are for example jars, bottles or also tetrapacks, wherein the container is designed for example with a dispensing and metering device.

Also provided herein are methods for temporarily deforming keratinic fibers, in particular human hair, using any of the cosmetic agents described above. On application, the cosmetic agent may be in powder form or comprise an aqueous cosmetic carrier. Preferred aqueous cosmetic carriers are aqueous, alcoholic or aqueous/alcoholic media preferably comprising at least about 10 wt. % water, relative to the total agent. Alcohols which may be present are in particular the lower alcohols with 1 to 4 carbon atoms such as for example ethanol and isopropanol which are conventionally used for cosmetic purposes.

Also provided herein are methods for cosmetic treatment of human hair, in which any cosmetic agent described herein is applied to optionally damp hair and left on the hair.

In an exemplary embodiment, a method for the cosmetic treatment of human hair includes:

(i) moistening a surface used as an application aid, (ii) applying a pulverulent cosmetic agent provided herein to the moistened surface of the application aid, (iii) contacting the hair with the surface from (ii) for application of said moistened cosmetic agent and arranging the hair in a hairstyle, (iv) drying the hair, with the proviso that the hair is not rinsed after step (iii).

Examples of application aids for applying the pulverulent composition are the hand, a paintbrush, a sponge, a cloth, a hair brush, a curved brush, a curler, a mascara brush or a comb. In an exemplary embodiment, it is preferred for the application aid surface used to be the palm of a hand.

Contacting the hair according to step (iii) involves for example targeted rubbing of the powder into the hair, combing or brushing.

Arranging the hair in a hairstyle according to step (iii) may proceed in a single operation with the application of said at least one pulverulent, hair-cosmetically active compound.

Drying the hair in step (iv) may proceed through drying using the indoor atmosphere or for example through hot air from a hairdryer.

In another preferred embodiment, a method for the cosmetic treatment of human hair includes:

(i) moistening the hair, (ii) applying a pulverulent cosmetic agent provided herein to the damp hair, (iii) arranging the hair into a hairstyle, (iv) drying the hair, with the proviso that the hair is not rinsed after step (ii).

Moistening of the hair in step (i) may proceed through spraying a liquid, preferably water, onto the fibers. The fibers in step (i) are preferably shampooed with a conventional shampoo, rinsed and then rubbed with a hand towel.

After completion of the rubbing step, the hair is not dripping wet but remains perceptibly damp.

The pulverulent composition is applied onto the hair according to step (ii) in metered manner for example using a salt shaker-like dispensing system.

Arrangement in a hairstyle according to step (iii) may proceed in a single operation with the application of said at least one pulverulent, hair-cosmetically active compound.

Drying in step (iv) may proceed through drying using the indoor atmosphere or for example through hot air from a hairdryer.

The preferred embodiments of the cosmetic agents described herein also apply mutatis mutandis to the methods for temporarily deforming keratinic fibers, and methods for cosmetic treatment of human hair.

Examples

1. Production of Pulverulent Styling Agents

As described below, the exemplary pulverulent styling agents 1 to 10 were produced, wherein they had the following compositions:

| Raw material | Invention 1 | Invention 2 | Invention 3 | Invention 4 | Invention 5 |
|---|---|---|---|---|---|
| Sepinov ® EMT 10, powder | 90.0 | 15.0 | 20.0 | 15.0 | 17.5 |
| Advantage ® S, powder | 10.0 | 85.0 | 80.0 | 60.0 | 81.9 |
| Perfume | — | — | — | — | 0.6 |

| Raw material | Invention 6 | Invention 7 | Invention 8 | Invention 9 | Invention 10 |
|---|---|---|---|---|---|
| Sepinov ® EMT 10, powder | 17.5 | 20.0 | 22.5 | 20.0 | 20.0 |
| Advantage ® S, powder | 82.0 | 79.5 | 77.0 | 78.8 | 78.8 |
| Perfume | 0.5 | 0.5 | 0.5 | 1.2 | 1.2 |

All the pulverulent raw materials were ground individually in a grinder. The raw materials were then mixed appropriately. The resultant finished styling powder was introduced into polyethylene bottles.

2.0. Application 2.1 to Damp Hair

Ten strands of hair were treated, each with one of the above-stated styling agents. To this end, the strands of hair were moistened and the agent was applied to the damp strands and rubbed in. The treated strands of hair were stretched out on a board, fixed thereto and left to dry.

With the exemplary compositions 1 to 10, the strands held their shape excellently. The hair clearly had more structure and texture. Despite the particulate raw materials used, no visible dulling of the hair was observed. The hair retained its natural gloss.

2.2 To Dry Hair

Ten strands of hair were treated, each by application by hand of one of the above-stated styling agents. To this end, the palm of the hand was moistened with water and the agent was rubbed onto the damp palm forming a gel. The resultant gel was applied to the strands of hair and rubbed in. The treated strands of hair were stretched out on a board, fixed thereto and left to dry.

The hair clearly had more structure and texture. Despite the particulate raw materials used, no visible dulling of the hair was observed. The hair retained its natural gloss.

3. List of Raw Materials Used

The raw materials used in the context of the Examples are defined as follows:

Sepinov EMT 10, Copolymer of 2-hydroxyethyl acrylate and 2-methyl-2-(1-powder oxo-2-propenyl)amino)-1-propanesulfonic acid monosodium salt (INCI name: Hydroxyethyl Acrylate/Sodium acryloyl dimethyl Taurate Copolymer) (Seppic)

Advantage S, powder Vinylcaprolactam/vinylpyrrolidone/dimethylaminoethyl methacrylate copolymer (INCI name: Vinyl Caprolactam/VP/Dimethylaminoethyl Methacrylate Copolymer) (ISP)

The invention claimed is:

1. A powder consisting of:
   (a) at least one polymer comprising at least one structural unit of formula (I) and at least one structural unit of formula (II),

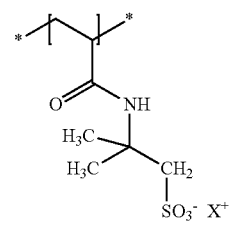

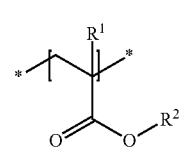

in which $X^+$ denotes a physiologically acceptable cation,
   $R^1$ denotes a hydrogen atom or a methyl group and
   $R^2$ denotes a hydroxyalkyl group, and
   (b) at least one setting polymer;
   wherein the volume-related average particle diameter ($d_{0.5}$) of the powder is 10 μm to 800 μm.

2. The powder according to claim 1, wherein $R^2$ denotes a 2-hydroxyethyl group.

3. The powder of claim 1, wherein, relative to the total weight of the composition, the at least one polymer of (a) is present in a quantity of 5 to 95 wt. %.

4. The powder according to claim 1, wherein the setting polymer of (b) is selected from polymers comprising at least one lactam structural unit.

5. The powder according to claim 1, wherein the setting polymer of (b) comprises at least one structural unit of formula (III) and at least one structural unit of formula (IV),

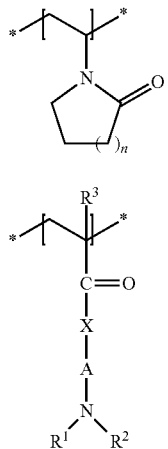

in which n denotes 1, 2 or 3,
$R^1$ and $R^2$ independently from each other denote a $C_1$ to $C_6$ alkyl group,
A denotes ethane-1,2-diyl or propane-1,3-diyl,
X denotes an oxygen atom or an NH group,
$R^3$ denotes a hydrogen atom or methyl group.

6. The powder according to claim 1, wherein, relative to the total weight of the composition, the setting polymer of (b) is present in a quantity of 2.0 wt. % to 95 wt. %.

7. A method for the cosmetic treatment of human hair, comprising:
optionally wetting the hair with water, and
applying powder according to claim 1 to the hair wherein the powder is not rinsed from the hair after being applied.

8. The method for the cosmetic treatment of human hair according to claim 7, wherein
the hair is moistened with water prior to applying the powder to the hair, and the method further comprising exposing the hair to mechanical stress after application of the powder to hair, and drying the hair.

9. The method for the cosmetic treatment of human hair according to claim 7, wherein
applying the powder with a moistened surface and contacting the moistened surface with the hair and styling the hair
the method further comprising drying the hair.

10. The method according to claim 9, herein the moistened surface is a moistened palm of a hand.

11. The powder of claim 1, wherein $R^2$ is a $C_2$ to $C_6$ hydroxyalkyl group.

12. The powder of claim 3, wherein the at least one polymer of (a) is present in a quantity of 5 to 50 wt. %.

13. The powder of claim 3, wherein the at least one polymer of (a) is present in a quantity of 10 to 30 wt. %.

14. The powder of claim 6, wherein the setting polymer of (b) is present in a quantity of 5.0 wt. % to 95.0 wt. %.

15. The powder according to claim 1, wherein the volume-related average particle diameter ($d_{0.5}$) of the powder is 25 μm to 500 μm.

* * * * *